US00PP27814P2

(12) United States Plant Patent
Horvath

(10) Patent No.: US PP27,814 P2
(45) Date of Patent: Mar. 28, 2017

(54) ***VERONICA* PLANT NAMED 'SPIKE'**

(50) Latin Name: ***Veronica* hybrid**
Varietal Denomination: Spike

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 111 days.

(21) Appl. No.: 14/544,277

(22) Filed: Dec. 19, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

Floridata. Floridata Plant Encyclopedia *Veronica spicata*, retrieved on Jun. 6, 2016, retrieved from the Internet at <http://floridata.com/Plants/Scrophulariaceae/Veronica%20spicata/1183> 5 pp.*

* cited by examiner

*Primary Examiner* — June Hwu

(57) ABSTRACT

A new, distinct *Veronica* plant as described and illustrated, characterized by the combination of longer stems, longer blue flower spikes, and cleaner foliage compared to the seed parent.

1 Drawing Sheet

Latin name: *Veronica* hybrid.
Cultivar name: 'Spike'.

BACKGROUND OF THE INVENTION

The present invention relates to a new and distinct hybrid of *Veronica* plant named 'Spike' characterized by the combination of longer stems, longer blue flower spikes, and cleaner foliage compared to the seed parent. The new *Veronica* was raised as a seedling from open pollinated seed sown from the seed parent *Veronica spicara nana*, not patented, in Hebron, Ill. in 2009. The male, pollen parent is unknown and was selected as a chance seedling. The selection of the new plant was due to the combination of longer stems, longer blue flower spikes, and cleaner foliage compared to the seed parent. Initial asexual reproduction has taken place at a nursery in Hebron, Ill. since 2010 by means of division, and vegetative stem cuttings. Continued asexual propagation by division and vegetative stem cuttings since that time has shown that the unique features of the new *Veronica* plant are stable and reproduced true to type in successive generations.

SUMMARY OF THE INVENTION

The new *Veronica* plant named 'Spike' characterized by combination of longer stems, longer blue flower spikes, and cleaner foliage compared to the seed parent have been observed to be unique and stable. For purpose of comparison the new plant will be referred to as 'Spike'.

Plants of 'Spike' can be compared to the seed parent plant of *Veronica spicata nana*, not patented. 1. The 'Spike' plant is taller growing to 40 cm while *Veronica spicata nana* grows to 20 cm. 2. The 'Spike' plant has longer inflorescence growing to 23 cm in length while *Veronica spicata nana* inflorescence grow to 10 cm in length.

Plants of 'Spike' can also be compared to another *Veronica spicata* 'Glory', U.S. Plant Pat. No. 18,932, patented. 1. The 'Spike' plant has longer inflorescence growing to 23 cm in length, while *Veronica spicata* 'Glory' inflorescence grow to 2-15 cm in length. 2. The 'Spike' plant has a flower color of RHS 99 B while *Veronica spicata* 'Glory' has a flower color of N 88 A to N 89 A.

DESCRIPTION OF PHOTOGRAPHS

Figure 1:
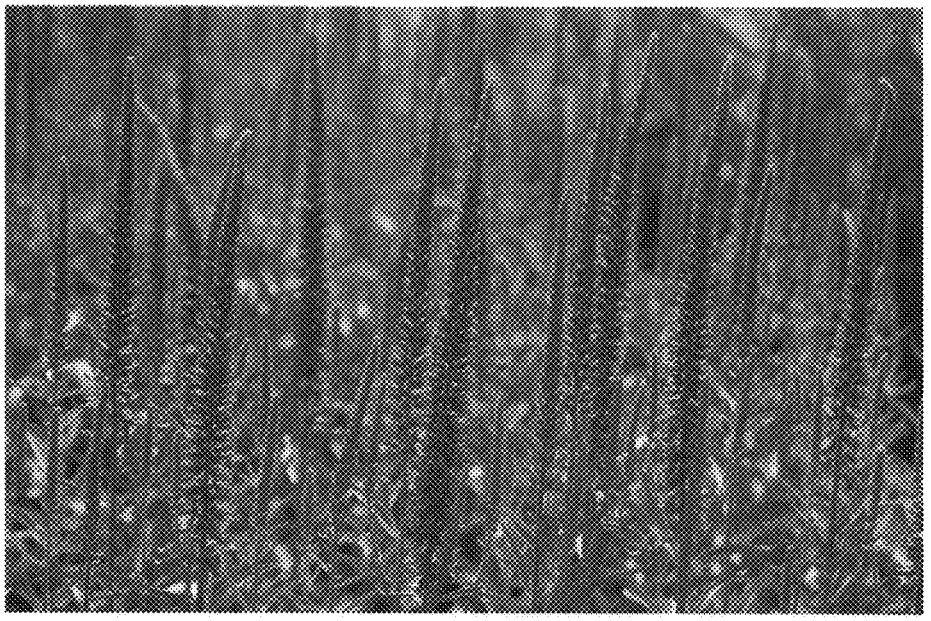
Figure 2:
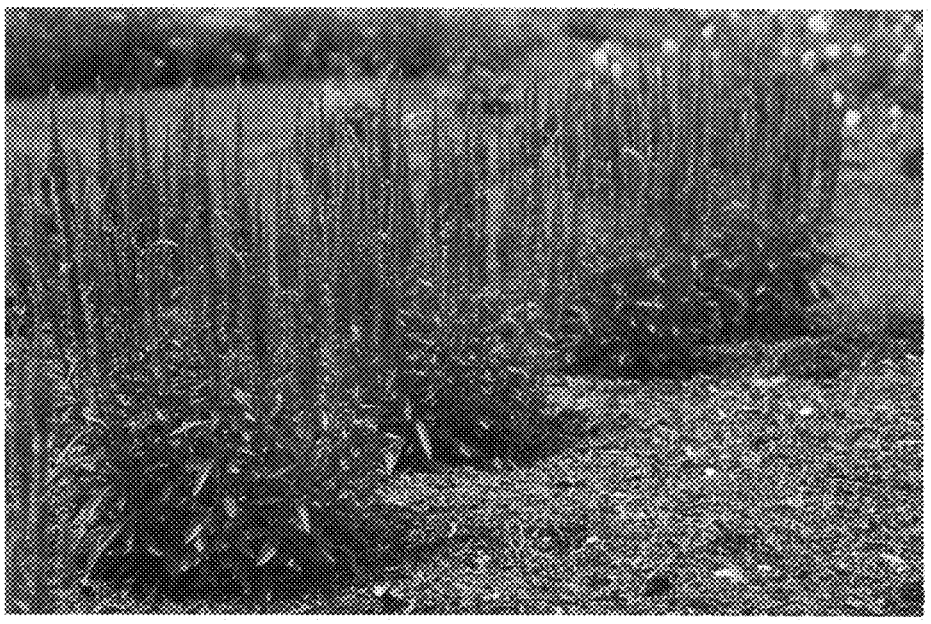

Plants pictured in the drawing were grown for two years.
FIG. 1. Close up of the flower spike.
FIG. 2. A group of plants.

DETAILED BOTANICAL DESCRIPTION

In the following description, color references are made to The Royal Horticultural Society Colour Chart (2001). Plants used for the description were grown for two years at a nursery in Hebron, Ill. Measurements and numerical values represent averages of typical plants.

Plant:
- *Botanical classification.*—*Veronica* hybrid.
- *Parentage.*—Female (seed parent) *Veronica spicata nana*, Male parent, unknown.
- *Form.*—Upright.
- *Plant height.*—40 cm from soil to top of flowers; width: 70 cm wide.
- *Growth.*—Herbaceous perennial, broad upright, moderate vigor.
- *Roots.*—Fibrous.

Stem:
- *Form.*—Cylindrical, branching from the base, no pinching required.
- *Color.*—144 A at the base, 144 D at the top half.
- *Surface texture.*—Glabrous.

*Length.*—40 cm.
*Diameter.*—4 mm wide.
*Flower stem internode length.*—2.5 cm.
*Internode quantity.*—Up to 6 flowering lateral branches.

Foliage:
*Arrangement.*—Opposite.
*Number of leaves per basal stem.*—16, 8 pairs.
*Size of leaf.*—Length: 6 cm on average, decreasing in both length and width distally. Width: 2.5 cm.
*Shape of leaf.*—Lanceolate.
*Shape of tip.*—Acute.
*Shape of base.*—Rounded to slightly attenuate.
*Texture.*—Glabrous.
*Margin type.*—Serrate.
*Color.*—Young and Mature leaves: Upper surface: 139 A. Lower surface: close to 137 C.
*Petioles.*—Glabrous. Length: 2 cm on average for lower leaves; 1 cm or less on average for other leaves. Diameter: 2 mm. Color: Adaxial 144 A, Abaxial 144 D.

Surface: Adaxial glabrous, Abaxial glabrous.
*Veins.*—Pattern: Pinnate with a pronounced mid-vein on the lower surface and depressed on the upper leaf surface. Color: Upper surface: 139 A. Lower surface: 137 C.

Flower:
*Natural flowering season.*—Continuous from mid to late June into July. Inflorescence type and habit: branched, terminal spike, no fragrance, flowers last about 5 days on plant.
*Rate of flower opening.*—About 25% of flowers open at once, all flowers open in about 4 weeks.

Type of flower: Tubular with four petal lobes.

Number of flowers: About 300 per spike; about 150 per lateral branch.

Inflorescence size:
*Diameter of a branched inflorescence.*—5 cm.
*Height.*—23 cm.
*Length of terminal spike.*—23 cm.
*Individual flower size.*—4 mm long, 2 mm wide.

Peduncle:
*Length.*—20 cm with secondary peduncles 3 cm long.
*Diameter.*—2 mm.
*Color.*—144 B with some aging to N 79 A.
*Orientation.*—Upright with 4-5 secondary peduncles at 30-45°.
*Strength.*—Strong.
*Surface.*—Glabrous.

Pedicel:
*Length.*—1-2 mm long, less than 1 mm wide, close to 0.5 mm.
*Color.*—146 D.

Petals:
*Petal arrangement.*—One larger above three slightly smaller.
*Large petal size.*—4 mm long; 2 mm wide.
*Small petal size.*—2 mm long; 1 mm wide.
*Margin.*—Entire.
*Tip shape.*—Emarginate upper lip; rounded lower lip.
*Length.*—Average upper lip: 4 mm; average lower lip: 2 mm.
*Width.*—Average upper lip: 2 mm; average lower lip: 1 mm.
*Petal quantity.*—4.
*Petal texture.*—Glabrous.
*Corolla.*—Length: 3 mm long, width: 2 mm wide, Color: 99 B.
*Petals.*—When opening: Upper surface: 99 13. Lower surface: 99 C. Fully opened: 99 B. Lower surface: 99 C.

Bud:
*Shape.*—Convolute, narrowly oblong, obtuse apex.
*Length.*—6 mm. and.
*Diameter.*—2 mm.
*Color.*—141 B and C.

Calyx:
*Arrangement.*—4 sepals fused into a tube at 70% of the length; 2 upper sepals fused nearly at the tips; 2 lower sepals fused nearly at the tips.
*Height.*—5 mm.
*Diameter.*—2 mm.
*Shape.*—Tubular.
*Sepals.*—Shape: ovate, acute apex, base fused forming corolla. Size: Average 4 mm long; 1 mm wide. Margin: Entire. Texture: glabrous. Color: Outer surface: 137 C at the top half and green 139 C at the base. Inner surface: from the tips down 137 D to 139 D at the base.
*Bracts.*—None observed.

Reproductive organs:
*Stamens.*—Number. — 2. Filament length. — 4 mm. Anthers. — Shape: Basifixed, elliptic. Length: 2 mm. Width 1 mm. Color: N 87 A. Pollen. — Color: white 155 C Amount: low.
*Pistil.*—Number. — One. Length. — 9 mm, less than 1 mm wide. Style. — Length: 12 mm. Color: 77 A at the top half fading to white at the base. Stigma — Shape: cylindrical. Color 77 A. Ovary color: initially green close to 139 D.

Seeds: Yes brown and round 2 mm long and 2 mm wide, color 144 B with parts N 79 B in color.

Disease/pest resistance: No unusual susceptibility to diseases or pests has been noted to date.

Temperature tolerance: Tolerate to heat at least up to 30° C. and cool at least down to USDA Zone 4-8.

I claim:

1. A new, distinct *Veronica* plant as described and illustrated, characterized by the combination of longer stems, longer blue flower spikes, and cleaner foliage compared to the seed parent.

* * * * *